(12) United States Patent
Nigam et al.

(10) Patent No.: US 7,074,552 B1
(45) Date of Patent: Jul. 11, 2006

(54) METHOD OF FORMING VASCULARIZED KIDNEY TISSUE

(75) Inventors: Sanjay Kumar Nigam, Del Mar, CA (US); Jizeng Qiao, Lexington, MA (US); Hiroyuki Sakurai, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 174 days.

(21) Appl. No.: 09/595,195

(22) Filed: Jun. 16, 2000

(51) Int. Cl.
*C12N 5/06* (2006.01)

(52) U.S. Cl. .................. 435/1.1; 435/373; 435/375; 435/325; 435/397; 435/369; 435/371; 424/93.1; 424/93.7

(58) Field of Classification Search ............... 435/377, 435/373, 1.1, 325, 397, 352, 369, 371, 375; 424/93.1, 93.7
See application file for complete search history.

(56) References Cited

U.S. PATENT DOCUMENTS 5,882,923 A * 3/1999 Sariola et al. ............... 435/325
6,060,270 A * 5/2000 Humes ....................... 435/69.1

OTHER PUBLICATIONS

Qiao, et al., "Branching morphogenesis independent of mesenchymal-epithelial contact in the developing kidney", *Proc. Natl. Acad. Sci.*, vol. 96, pp. 7330-7335, Jun. 1999.
Santos, et al., "Modulation of HGF-Induced Tubulogenesis and Branching by Multiple Phosphorylation Mechanisms", *Developmental Biology*, vol. 159, pp. 535-548, 1993.
Santos, et al., "HGF-Induced Tubulogenesis and Branching of Epithelial Cells is Modulated by Extracellular Matrix and TGF-β", *Developmental Biology*, vol. 160, pp. 293-302, 1993.

(Continued)

*Primary Examiner*—Leon B. Lankford, Jr.
*Assistant Examiner*—Allison M. Ford
(74) *Attorney, Agent, or Firm*—Buchanan Ingersoll LLP

(57) ABSTRACT

A method for constructing a stable bioactive mammalian embryonic kidney is described herein. A kidney so constructed requires no artificial support, nor porous man made membranes or tubing to effectuate its biological function of filtering body fluids. A single donor embryonic kidney, or fragment thereof, can produce a great number of functional kidneys suitable for treating subjects with various kidney disorders. It is anticipated that said in vitro produced kidney would be less, or not at all, antigenic when transplanted into a subject, because of its embryonic character and artificial propagation in culture. This method of producing a functional organ can be useful in cloning other organ structures containing inducible epithelial tissues.

5 Claims, 11 Drawing Sheets

OTHER PUBLICATIONS

Santos, et al., "Involvement of Hepatocyte Growth Factor in Kidney Development", *Developmental Biology*, vol. 163, pp. 525-529, 1994.

Barros, et al., "Differential tubulogenic and branching morphogenetic activities of growth factors: Implications for epithelial tissue development", *Proc. Natl. Acad. Sci.* vol. 92, pp. 4412-4416, May 1995.

Pavlova, et al., "Evolution of gene expression patterns in a model of branching orphogenesis", *Am. J. Physiol. Renal Physiol.*, vol. 277, pp. F650-F663, 1999.

Grobstein, et al., "Inductive Epithelio-mesenchymal Interaction in Cultured Organ Rudiments of the Mouse", *Science*, vol. 118, No. 3053, pp. 52-55, Jul. 3, 1953.

Grobstein, "Morphogenetic Interaction between Embryonic Mouse Tissues separated by a Membrane Filter", *Nature*, vol. 172, pp. 869-871, Jul. 4, 1953-Dec. 26, 1953.

Grobstein, et al., "Inductive Interaction in the Development of the Mouse Metanephros", *The Journal of Experimental Zoology*, vol. 130, pp. 319-339, Oct., Nov., Dec. 1955.

Saxen, *Organogenesis of the Kidney*, (table of contents) Cambridge University Press, Cambridge, 1987.

Davies, et al., "Inductive Interactions between the Mesenchyme and the Ureteric Bud", *Experimental Nephrology*, vol. 4, pp. 77-85, Mar.-Apr. 1996.

Vainio, et al., "Inductive Tissue Interactions, Cell Signaling and the Control of Kidney Organogenesis", *Cell*, vol. 90, pp. 975-978, Sep. 19, 1997.

Schofield, et al., "Growth Factors and Metanephrogenesis", *Experimental Nephrology*, vol. 4, pp. 97-104, Mar.-Apr. 1996.

Nigam, "Determinants of branching tubulogenesis", *Current Opinion in Nephrology and Hypertension*, Vo. 4, No. 3, pp. 209-214, 1995.

Sakurai, et al., "*In vitro* branching tubulogenesis: Implications for developmental and cystic disorders, nephron number, renal repair, and nephron engineering", *Kidney International*, vol. 54, pp. 14-26, 1998.

Schuchardt, et al., "Defects in the kidney and enteric nervous system of mice lacking the tyrosine kinase receptor Ret", *Nature*, Vo. 367, pp. 380-383, Jan. 27, 1994.

Durbec, et al., "GDNF signalling through the Ret receptor tyrosine kinase", *Nature*, vol. 381, No. 6585, pp. 789-793, Jun. 27, 1996.

Sanchez, et al., "Renal agenesis and the absence of enteric neurons in mice lacking GDNF", *Nature*, vol. 382, No. 6586, pp. 70-73, Jul. 4, 1996.

Pichel, et al., "Defects in enteric innervation and kidney development in mice lacking GDNF", *Nature*, vol. 382, No. 6586, pp. 73-76, Jul. 4, 1996.

Moore, et al., "Renal and neuronal abnormalities in mice lacking GDNF", *Nature*, vol. 382, No. 6586, pp. 76-79, Jul. 4, 1996.

Pepicelli, et al., "Rapid Communication GDNF Induces Branching and Increased Cell Proliferation in the Ureter of the Mouse", *Developmental Biology*, vol. 192, pp. 193-198, 1997.

Sakurai, et al., "An *in vitro* tubulogenesis system using cell lines derived from the embryonic kidney shows dependence on multiple soluble growth factors", *Proc. Natl. Acad. Sci.*, vol. 94, pp. 6279-6284, Jun. 1997.

Cantley, et al., "Regulation of mitogenesis, motogenesis, and tubulogenesis hepatocyte growth factor in renal collecting duct cells", *American Journal of Physiology*, vol. 267, No. 2, pp. F271-F280, Aug. 1994.

Sakurai, et al., "EGF receptor ligands are a large fraction of in vitro branching morphogens secreted by embryonic kidney", *Am. J. Physiol.* vol. 273, No. 3, pp. F463-F472, Sep. 1997.

Gumbiner, "Eithelial Morphogenesis", *Cell*, vol. 69, pp. 385-387, May 1, 1992.

Rodriguez-Boulan, et al., "Morphogenesis of the Polarized Epithelial Cell Phenotype", *Science*, vol. 245, pp. 718-725, Aug. 18, 1989.

Sukhatme, "Renal Development: Challenge and Opportunity", *Seminars in Nephrology*, vol. 12, No. 4, pp. 422-426, Sep. 1993.

Vega, et al., "Glial cell line-derived neurotrophic factor activates the receptor tyrosine kinase RET and promotes kidney morphogenesis", *Proc. Natl. Acad. Sci.*; vol. 93, pp. 10657-10661, Oct. 1996.

Sainio, et al., "Glial-cell-line-derived neurotrophic factor is required for bud initiation from ureteric epithelium", *Development*, vol. 124, pp. 4077-4087, Oct. 1997.

Kuznetsov, et al., "Perturbations in maturation of secretory proteins and their association with endoplasmic reticulum chaperones in a cell culture model for epithelial eschemia", *Proc. Natl. Acad. Sci.*, vol. 93, pp. 8584-8589, Aug. 1996.

Molitoris, et al., "Role of the actin cytoskeleton in ischemia-induced cell injury and repair", *Pediatric Nephrol.*, vol. 11, pp. 761-767. 1997.

Bush, et al., "Selective degradation of E-cadherin and dissolution of E-cadherin-catenin complexes in epithelial ischemia", *Am. J. Physiol. Renal Physiol.*, vol. 278, pp. F847-852, 2000.

Bush, et al., "Pretreatment with inducers of ER molecular chaperones protects epithelial cells subjected to ATP depletion", *Am. J. Physiol. Renal Physiol.*, vol. 277, pp. F211-218, 1999.

Hammerman, et al., "Acute renal failure. III. The role of growth factors in the process of renal regeneration and repair", *Am. J. Physiol. Renal Physiol.*, vol. 279, pp. F3-F11, 2000.

Steinberg, et al., "Cadherins and their connections: adhesion junctions have broader functions", *Curr. Opin. Cell Biol.*, vol. 11, No. 5, pp. 554-560, Oct. 1999.

Le, et al., "Recycling of E-Cadherin: A Potential Mechanism for Regulating Cadherin Dynamics", *The Journal of Cell Biology*, vol. 146, No. 1, pp. 219-232, Jul. 12, 1999.

Denker, et al., "Molecular structure and assembly of the tight junction", *Am. J. Physiol. Renal Physiol*, vol. 274, pp. F1-F9, 1998.

Tsukamoto, et al., "Role of tyrosine phosphorylation in the reassembly of occludin and other tight junction proteins", *Am. J. Physiol. Renal Physiol.*, vol. 276, pp. F737-750, 1999.

Ye, et al., "A role for intracellular calcium in tight junction reassembly after ATP depletion-repletion", *Am. J. Physiol. Renal Physiol.*, vol. 277, pp. F524-F532, 1999.

Nigam, et al., "A Set of Endoplasmic Reticulum Proteins Possessing Properties of Molecular Chaperones Includes $Ca^{2+}$-binding Proteins and Members of the Thioredoxin Superfamily", *The Journal of Biological Chemistry*, vol. 269, No. 3, pp. 1744-1749, Jan. 21, 1994.

Bush, et al., "Proteasome Inhibition Leads to a Heat-shock Response, Induction of Endoplasmic Reticulum Chaperones, and Thermotolerance", *The Journal of Biological Chemistry*, vol. 272, No. 14, pp. 9086-9092, Apr. 4, 1997.

Dong, et al., "Intracellular $CA^{2+}$ Thresholds That Determine Survival or Death of Energy-Deprived Cells", *American*

Journal of Pathology, vol. 152, No. 1, pp. 231-240, Jan. 1998.

Kribben, et al., "Evidence for Role of Cytosolic Free Calcium in Hypoxia-Induced Proximal Tubule Injury", *J. Clin. Invest.*, vol. 93, pp. 1922-1929, May 1994.

Liu, et al., "Endoplasmic Reticulum Stress Proteins Block Oxidant-induced $CA^{2+}$ Increases and Cell Death", *The Journal of Biological Chemistry*, vol. 273, No. 21, pp. 12858-12862, May 22, 1998.

Yu, et al., "The Endoplasmic Reticulum Stress-Responsive Protein GRP78 Protects Neurons Against Excitotoxicity and Apoptosis: Suppression of Oxidative Stress and Stabilization of Calcium Homeostasis", *Experimental Neurology*, vol. 155, No. 2, pp. 302-314, Feb. 1999.

Bian, et al., "Roles of Cytoplasmic $Ca^{2+}$ and intracellular $CA^{2+}$ stores in induction and suppression of apoptosis in S49 cells", *American Journal of Physiology*, vol. 272, No. 4, pp. C1241-1249, Apr. 1997.

Bush, et al., "Genesis and reversal of the ischemic phenotype in epithelial cells", *The Journal of Clinical Investigation*, vol. 106, No. 5, pp. 621-626, Sep. 2000.

Milner, et al., "A Novel 17 kD Heparin-Binding Growth Factor (HBGF-8) in Bovine Uterus: Purification and N-Terminal Amino Acid Sequence", *Biochemical and Biophysical Research Communications*, Vp;/ 165, No. 3, pp. 1096-1103, Dec. 29, 1989.

Mitsiadis, et al., "Expression of the heparin-binding cytokines, midkine (MK) and HB-GAM (pleiotrophin) is associated with epithelial-mesenchymal interactions during fetal development and organogenesis", *Development*, vol. 121, pp. 37-51, 1995.

Sato, et al., "Pleiotrophin as a Swiss 3T3 Cell-Derived Potent Mitogen for Adult Rat Hepatocytes", *Experimental Cell Research*, vol. 246, No. 1, pp. 152-164, Jan. 10, 1999.

Kurtz, et al., "Pleiotrophin and Midkine in Normal Development and Tumor Biology", *Critical Reviews in Oncogenesis*, vol. 6, No. 2, pp. 151-177, 1995.

Rauvala, et al. "Expression of HB-GAM (heparin-binding growth-associated molecules) in the pathways of developing axonal processes in vivo and neurite outgrowth in vitro induced by HB-GAM" *Developmental Brain Research*, Voll. 79, pp. 157-176, 1994.

Imai, et al., Osteoblast Recruitment and Bone Formation Enhanced by Cell Matrix-associated Heparin-binding Growth-associated Molecule (HB-GAM), *The Journal of Cell Biology*, vol. 143, No. 4, pp. 1113-1128, Nov. 16, 1998.

Tomita, et al, "Direct in Vivo Gene Introduction into Rat Kidney", *Biochemical and Biophysical Research Communications*, vol. 186, No. 1, pp. 129-134, Jul. 15, 1992.

Zhu, et al., "Systemic Gene Expression After Intravenous DNA Delivery into Adult Mice", *Science*, vol. 261, pp. 209-211, Jul. 9, 1993.

Moullier, et al., "Adenoviral-mediated gene transfer to renal tubular cells *in vivo*", *Kidney International*, vol. 45, pp. 1220-1225, 1994.

Montesano, et al., "Induction of Epithelial tubular Morphogenesis in Vitro by Fibroblast-Derived Soluble Factors", *Cell*, vol. 66, pp. 697-711, Aug. 23, 1991.

Bladt, et al., "Essential role for the c-met receptor in themigration of myogenic precursor cells into the limb bud", *Nature*, vol. 376, No. 6543, pp. 68-771, Aug. 31, 1995.

Schmidt, et al., "Scatter factor/hepatocyte growth factor is essential for liver development", *Nature*, vol. 373, No. 6516, pp. 699-702, Feb. 23, 1995.

Schuchardt, et al., "Renal agenesis and hypodysplasia in ret-k- mutant mice result from defects in ureteric bud development", *Development*, vol. 122, No. 6, pp. 1919-1929, Jun. 1996.

Metzger, et al., "Genetic Control of Branching Morphogenesis", *Science*, vol. 284, pp. 1635-1639, Jun. 4, 1999.

Ohuchi, et al., "FGF10 Acts as a Major Ligand for FGF Receptor 2 IIIb in Mouse Multi-Organ Development", *Biochemical and Biophysical Research Communications*, vol. 277, No. 3, pp. 643-649, Nov. 2, 2000.

Bullock, et al., "Renal agenesis in mice homozygous for a gene trap mutation in the gene encoding heparan sulfate 2-sulfotransferase", *Genes & Development*, vol. 12, No. 12, pp. 1894-1906, Jun. 15, 1998.

Bullock, et al., "Developmental and species differences in the response of the ureter to metabolic inhibition", *European Journal of Physiology*, vol. 436, No. 3, pp. 443-448, Aug. 1998.

Davies, et al., "Sulphated proteoglycan is required for collecting duct growth and branching but not nephron formation during kidney development", *Development*, vol. 121, Issue 5, pp. 1507-1517, 1995.

Kispert, et al., "Proteoglycans are required for maintenance of Wnt-11 expression in the ureter tips" *Development*, vol. 122, pp. 3627-3637, 1996.

Montesano, et al., "Identification of a Fibroblast-Derived Epithelial Morphogen as Hepatocyte Growth Factor", *Cell*, vol. 67, No. 5, pp. 901-908, Nov. 29, 1991.

Zelzer, et al., "Cell fate choices in *Drosophila* tracheal morphogenesis", *BioEssays*, vol. 22, No. 3, pp. 219-226, Mar. 2000.

Enomoto, et al., "GFRα-1 Deficient Mice Have Deficits in the Enteric Nervous System and Kidneys", *Neuron*, vol. 21, No. 2, pp. 317-324, Aug. 1998.

Imai, et al., "Towards gene therapy for renal diseases", *Nephrologie*, vol. 18, No. 7, pp. 397-402, 1998.

Imai, et al., "Gene transfer and kidney disease", *Journal of Nephrology*, vol. 11, No. 1, pp. 16-19, Jan.-Feb. 1998.

Imai, et al., "Strategies of gene transfer fo the kidney", *Kidney*, vol. 53, No. 2, pp. 264-272, Feb. 1998.

Meng, et al., "Pleiotrophin signals increased tyrosine phosphorylation of β-catenin through inactivation of the intrinisic catalytic activity of the receptor-type protein tyrosine phosphatase β/ζ", *Proc. Natl. Acad. Sci.*, vol. 97, No. 6, pp. 2603-2608, Mar. 14, 2000.

Vainio, et al., "Epithelial-Mesenchymal Interactions Regulate the Stage-Specific Expression of a Cell Surface Proteoglycan, Syndecan, in the Developing Kidney", *Developmental Biology*, vol. 134, No. 2, pp. 382-391, Aug. 1989.

Vainio, et al., "Syndecan and Tenascin Expression is Induced by Epithelial-Mesenchymal Interactions in Embryonic Tooth Mesenchyme", *The Journal of Cell Biology*, vol. 108, No. 5, pp. 1945-1954, May 1989.

Ohuchi, et al., "Renal tubular effects of endothelin-B receptor signaling: its role in cardiovascular homeostasis and extracellular volume regulation", *Curr Opin Nephrol Hyperten.*, vol. 9, No. 4, pp. 435-439, Jul. 2000.

Thadhani, et al., "Acute renal failure", *The New England Journal of Medicine*, vol. 334, No. 2, pp. 1448-1460, May 30, 1996.

Bonventre, et al., "Acture renal failure. I. Relative importance of proximal vs. distal tubular injury", *Am. J. Physiol*, vol. 275, No. 5, pp. F623-F631, Nov. 1998.

Molitoris, et al., "Acute renal failure. II. Experimental models of acute renal failure: imperfect but indispensable", *Am. J. Physiol. Renal Physiol.*, vol. 278, No. 1, pp. F1-F12, Jan. 2000.

Fish, et al., "Alterations of Epithelial Polarity and the Pathogenesis of Disease States", *The New England Journal of Medicine*, vol. 330, No. 14, pp. 1580-1588, Apr. 7, 1994.

Tsukamoto, et al., "Tight Junction Proteins Form Large Complexes and Associate with the Cytoskeleton in an ATP Depletion Model for Reversible Junction Assembly", *The Journal of Biological Chemistry*, vol. 272, No. 26, pp. 16133-16139, Jun. 27, 1997.

Hammerman, et al., "Acute renal failure. III. The role of growth factors in the process of renal regeneration and repair", *Am. J. Physiol. Renal Physiol.*, vol. 279, No. 1, pp. F3-F11, Jul. 2000.

Gailit, et al., "Redistribution and dysfunction of integrins in cultured renal epithelial cells exposed to oxidative stress", *American Journal of Physiology*, vol. 264, No. 1, pp. F149-F157, Jan. 1993.

Lieberthal, et al., "β Integrin-Mediated Adhesion between Renal Tubular Cells after Anoxic Injury", *Journal of the American Society of Nephrology*, vol. 8, Issue 2, pp. 175-183, Feb. 1997.

Zuk, et al., "Polarity, integrin, and extracellular matrix dynamics in the postischemic rat kidney", *American Journal of Physiology*, vol. 275, No. 3, pp. C711-C731, Sep. 1998.

Gumbiner, et al., "The Role of the Cell Adhesion Molecule Uvomorulin in the Formation and Maintenance of the Epithelial Junctional Complex", *The Journal of Cell Biology*, vol. 107, No. 4, pp. 1575-1587, Oct. 1988.

McNeill, et al., "Novel Function of the Cell Adhesion Molecule Uvomorulin as an Inducer of Cell Surface Polarity", *Cell*, vol. 62, No. 2, pp. 309-316, Jul. 27, 1990.

Mandel, et al., "ATP depletion: a novel method to study junctional properties in epithelial tissues. II. Internalization of Na$^+$, K$^+$-ATPase and E-cadherin", *Journal of Cell Science*, vol. 107, Part 12, pp. 309-316, Dec. 1994.

Tsukita, et al., "Structural and signalling molecules come together at tight junctions", *Current Opinion in Cell Biology*, vol. 11, No. 5, pp. 628-633, Oct. 1999.

Denker, et al., "Molecular structure and assembly of the tight junction", *American Journal of Physiology*, vol. 274, No. 1, pp. F1-F9, Jan. 1998.

Gopalakrishnan, et al., "Rho GTPase signaling regulates tight junction assembly and protests tight junctions during ATP depletion", *American Journal of Physiology*, vol. 275, No. 3, pp. C798-C809, Sep. 1998.

Kuznetsov, et al., "Folding of Secretory and Membrane Proteins", *The New England Journal of Medicine*, vol. 339, No. 23, pp. 1688-1695, Dec. 3, 1998.

Van Why, et al., "Thresholds for cellular disruption and activation of the stress response in renal epithelia", *American Journal of Physiology*, vol. 277, No. 2, pp. F227-F234, Aug. 1999.

Gething, et al., "Protein folding in the cell", *Nature*, vol. 355, No. 6355, pp. 33-45, Jan. 1992.

Gabai, et al., "Rise in heat-shock protein level confers tolerance to energy deprivation", *FEBS Letters*, vol. 327, No. 3, pp. 247-250, Aug. 1993.

Georgopoulos, et al., "Role of the major heat shock proteins as molecular chaperones", *Annual Review of Cell Biology*, vol. 9, pp. 601-634, 1993.

Yoo, et al., "Anti-Inflammatory Effect of Heat Shock Protein Induction is Related to Stabilization of IκBα Through Preventing IκB Kinase Activation in Respiratory Epithelial Cells", *The Journal of Immunology*, vol. 164, No. 10, pp. 5416-5423, May 15, 2000.

Rauchman, et al., "An osmotically tolerant inner medullary collecting duct cell line from an SV40 transgenic mouse", *American Journal of Physiology*, vol. 265, No. 3, pp. F416-F424, Sep. 1993.

Barasch, et al., "A ureteric bud cell line induces nephrogenesis in two steps by two distinct signals", *American Journal of Physiology*, vol. 271, No. 1, pp. F50-F61, Jul. 1996.

Barasch, et al., "Ureteric bud cells secrete multiple factors, including bFGF, which rescue renal progenitors from apoptosis", *American Journal of Physiology*, vol. 273, No. 5, pp. F757-F767, Nov. 1997.

Laitinen, et al., "Changes in the Glycosylation Pattern During Embryonic Development of Mouse Kidney as Revealed with lectin Conjugates", *The Journal of Histochemistry and Cytochemistry*, vol. 35, No. 1, pp. 55-65, 1987.

Gilbert, et al., "Defect of Nephrogenesis Induced by Gentamicin in Rat Metanephric Organ Culture", *Laboratory Investigation*, vol. 70, No. 5, pp. 656-666, May 1994.

O'Rourke, et al., "Expression of c-ret promotes morphogenesis and cell survival in mIMCD-3 cells", *American Journal of Physiology*, vol. 276, No. 4, pp. F581-F589, Apr. 1999.

Al-Awqati, et al., "Architectural patterns in branching morphogenesis in the kidney", *Kidney International*, vol. 54, No. 6, pp. 1832-1842, Dec. 1998.

Liu, et al., "Comparative Role of Phosphotyrosine Kinase Domains of c-ros and c-ret Protooncogenes in Metanephric Development with Respect to Growth Factors and Matrix Morphogens", *Developmental Biology*, vol. 178, pp. 133-148, 1996.

Rauvala, et al., "An 18-kd heparin-binding protein of developing brain that is distinct from fibroblast growth factors", *The EMBO Journal*, vol. 8, No. 10, pp. 2933-2941, 1989.

Li, et al., "Cloning and Expression of a Developmentally Regulated Protein that Induces Mitogenic and Neurite Outgrowth Activity", *Science*, vol. 250, No. 4988, pp. 1690-1694, Dec. 21, 1990.

Vanderwinden, et al., "Cellular distribution of the new growth factor Pleiotrophin (HB-GAM) mRNA in developing and adult rat tissues", *Anat. Embryol.*, vol. 186, pp. 387-406, 1992.

Sweet, et al., "Impaired Organic Anion Transport in Kidney and Choroid Plexus of Organic Anion Transporter 3 (*Oat3* (*Slc22a8*)) Knockout Mice", *The Journal of Biological Chemistry*, vol. 277, No. 30, pp. 26934-26943, Jul. 26, 2002.

Sweet, et al., "The organic anion transporter family: from physiology to ontogeny and the clinic", *Am. J. Physiol. Renal Physiol.* vol. 281, pp. F197-F205, 2001.

Steer, et al. "A strategy for in vitro propagation of rat nephrons Rapid Communication", *Kidney International*, vol. 62, pp. 1958-1965, 2002.

Nigam, et al., "Toward an understanding of epithelial morphogenesis in health and disease", *Current Opinion in Nephrology and Hypertension*, vol. 1, pp. 187-191, 1992.

Sakurai, et al., "Identification of pleiotrophin as a mesenchymal factor involved in ureteric bud branching morphogenesis", *Development*, vol. 128, pp. 3283-3293, 2001.

* cited by examiner

METHOD OF FORMING VASCULARIZED KIDNEY TISSUE

BACKGROUND OF THE INVENTION

1. Field of the Invention

The present invention generally concerns a new method of engineering a kidney in vitro.

The present invention particularly concerns a new method and procedure for propagating cloned kidney members from embryonic ureteric bud tips grown in vitro under specific culture conditions.

2. Description of Related Art

Branching tubulogenesis is an essential mechanism by which epithelial tissues such as kidney, salivary gland and prostate develop (Proc. Natl. Acad. Sci. USA, 96, 7330–7335, 1999 incorporated herein by reference). Largely based on the classical studies of Brobstein and coworkers, direct interactions between mesenchymal and epithelial components of embryonic tissue have been thought to be crucial for branching morphogenesis in most epithelial tissues. During kidney development, for example, direct cell-cell interactions between the metanephric mesenchyme and the epithelial component, the ureteric bud (UB), are believed to be essential for branching morphogenesis of the latter. This view is based on the fact that it had not been possible, in many previous studies, to observe proliferation and branching of the UB in the absence of direct contact with the metanephric mesenchyme or another inducing tissue, suggesting that the developmental program necessary for branching depended upon direct contact between surface proteins of the UB with surface proteins of the metanephric mesenchyme. Further, no known soluble factor or set of factors had been able to induce UB branching morphogenesis in vitro.

This view has gained additional support from knockout experiments in which absent expression of a variety of individual soluble growth factors held to be important in kidney development, based upon previous organ culture experiments, fail to show defective branching morphogenesis of the UB. Nevertheless, recent studies have also shown that glial cell line derived neurotrophic factor (GDNF) is necessary for early UB outgrowth, but on its own, it fails to promote proliferation and branching morphogenesis of isolated UB in vitro. These results left open the possibility that some unknown soluble factor, or combination of factors, derived form the metanephric mesenchyme, might be sufficient to induce epithelial branching morphogenesis.

A wide array of renal and urological abnormalities are likely due to defective tubulogenesis and branching morphogenesis of the developing collecting system It is now clear that a variety of defects in the kidney and urinary collecting system are the result of abnormal development of these structures in the fetus. The spectrum of disease is huge, as is their potential morbidity. The molecular basis for these diseases is poorly understood; however, it appears, in many instances, that the problem lies in defective morphogenesis of the ureteric bud. The urinary collecting system (from the trigone of the bladder including ureteral orifices, ureters, renal pelvis, and collecting tubules) arises from the UB. Thus, developmental abnormalities of the UB and its derivatives would be expected to give rise to a variety of "urological" as well as "nephrological" clinical syndromes. Developmental anomalies extrinsic to the kidney, but in principle attributable to defects in UB morphogenesis, include vesicoureteral reflux (VUR), ureteropelvic junction obstruction (UPJO), ectopic and duplicated ureters. Since normal kidney development depends critically upon mutual inductive interactions between the UB and the metanephric mesenchyme (MM), inefficient or defective branching morphogenesis of the UB would be expected to result in various aplastic, hypoplastic, and perhaps dysplastic diseases. Extrinsic collecting system abnormalities would then be expected to, coexist with various hypoplastic diseases of the kidney. In fact, up to ⅓ of end stage renal disease in children is due to developmental problems, the majority of which may be categorized as ureteral with or with out dysplasia or hypoplasia of one or both kidneys. In addition, perhaps 5–10% of all adults has some occult developmental anomaly.

Recent advances in the molecular biology of kidney development demonstrate that specific molecular defects can explain a variety of clinical syndromes. VUR, UPJO, and various dysplastic, and hypoplastic kidney disorders have been known to co-exist and to be expressed in various human lineages with a variable penetrance, the so-called CAKUT syndrome. In addition, several targeted gene-deletion experiments have resulted in phenotypes that may be best characterized as resulting form defective UB morphogenesis (directly or indirectly). These range from the renal aplasia associated with complete UB failure associated with deletions of WT-1 and RTK c-ret molecules to more subtle effects resulting in hypoplasia or oligonephronia such as seen with certain integrin knockouts. Defective collecting system development may play a role in the most common congenital cystic disease, ADPKD. The inventors have shown that expression of PKD-1 correlates spatiotemporally with branching morphogenesis of the UB. Findings such as this have led to the hypothesis that ADPKD and other cystic diseases of the kidney result form defects in the developmental program necessary for proper tubulogenesis.

Aside from "congenital" disease per se, defective collecting system development may underlie predisposition to disease much later in life. It has been argued that low nephron number is crucial to the development of hypertension and chronic renal failure in adults. This may well be the result of defective branching morphogenesis during development of the urinary collecting system, because the degree of ureteric bud branching during collecting system development determines the number of nephrons in the adult kidney. Hence, aggregate nephron number is a function of factors regulating ureteric bud branching during urinary tract development. If one assumes a 1% decrement in efficiency of branching morphogenesis (99% efficient at all steps), this results in less than half the normal number of nephrons after the roughly 20 generations of branching which occur during human nephrogenesis.

In summary, a broad spectrum of disorders ranging from urological abnormalities, hypoplasia, dysplasia, and cystic diseases, and possibly even certain forms of "essential" hypertension, may be viewed as developmental diseases of ureteric bud and its derivatives. Recent work indicates that a molecular basis exists for these disorders and that much human morbidity and mortality may be attributable to varying degrees of failure in the process of ureteric bud branching morphogenesis.

The cellular and molecular basis of development of the urinary collecting system, particularly tubulogenesis and branching morphogenesis, are not well understood In the mouse, inductive interactions between the MM and the UB that are necessary for formation of the metanephric kidney take place around embryonic day 11; in the rat, this occurs around day 13. Through in vitro organ and cell culture studies, as well as knockouts, both soluble factor influence and cell—cell contact have been implicated, although the exact nature of the inducing signals is a topic of intense investigation and debate. Subsequent to these interactions, the metanephric mesenchyme undergoes a "mesenchymal to epithelial transition," during which it acquires epithelial markers such as cytokeratins. As development progresses, the recently epithelialized mesenchyme forms early nephronal structures, which ultimately develop into the proximal through distal tubule. All this appears to be guided by interactions with the ureteric bud as it, through a process of branching morphogenesis, develops into the collecting system. Thus, while the mesenchyme is differentiating, the ureteric bud is invading it and undergoing iterations of symmetric and asymmetric dichotomous branching. About 20 generations of such branching events result in the roughly 1 million collecting ducts that form the renal portion of the urinary collecting system.

This general process is not unique to the kidney. Branching tubulogenesis (ductogenesis) is an essential mechanism by which most, if not all, epithelial tissues form in the embryo. Largely due to the classical studies using organ culture, direct interactions between mesenchymal and epithelial components of embryonic tissue have been thought to be crucial for branching morphogenesis in kidney and urinary tract. This view is based on the fact that it had not been possible, in many previous studies, to observe proliferation and branching of the UB in the absence of direct contact with the metanephric mesenchyme or another inducing tissue, suggesting that the developmental program necessary for branching depended upon direct contact between surface proteins of the UB with surface proteins of the metanephric mesenchyme. Furthermore, no known soluble factor or set of factors had been able to induce UB branching morphogenesis in vitro. This view has gained additional support from knockout experiments in which absent expression of a variety of individual soluble growth factors held to be important in kidney development (based upon previous organ culture experiments) fail to show defective branching morphogenesis of the UB. Nevertheless, recent studies have demonstrated that glial cell line derived neurotrophic factor (GDNF) is necessary for early UB outgrowth, but as the inventors have shown, on its own, it fails to promote proliferation and branching morphogenesis of isolated UB in vitro (FIG. 6). [Proc. Natl. Acad. Sci., 96, 7330–7335, 1999 incorporated herein by reference].

The primary focus of this invention is to present a novel method and procedure for propagation of cloned kidney members from embryonic ureteric bud which also has applicability to other epithelial-derived tissues. This method differs in concept and substance from U.S. Pat. No. 6,060,270 (May 9, 2000) issued to Humes. In contrast to the Humes patent, this method employs the intrinsic ability of the embryonic epithelial tissue to branch in order to generate an indefinite number of organs from a single embryonic ureteric bud. Thus, in principle, after six generations of branching, a single ureteric bud can give rise to 256 ($2^8$) kidneys or even more, depending upon the number of generations the ureteric bud is allowed to branch in culture.

SUMMARY OF THE INVENTION

The primary object of this invention is to provide functioning replacement organs or functional fragments thereof that are suitable for transplanting into recipients suffering from a variety of life-threatening diseases or developmental anomalies.

Another object in accordance with the present invention is to generate functional mammalian epithelium-derived organs, or active fragments thereof from embryonic explants, tissues or cells utilizing in vitro culture techniques.

Another object of this invention is to define soluble inducing factors effective in transforming embryonic epithelial cells or tissues into regenerating functional organs, glands and the like.

A further, most preferred object is to provide a bank of embryonic organs and tissues capable of replacing diseased, or otherwise incapacitated vital organs and tissues, minimizing the need for matching donors and/or immunosuppressive drugs.

In accordance with these objects, this invention contemplates a method for constructing a functional mammalian tubulogenic organ or fragment thereof in vitro. The method involves culturing and propagating embryonic explants, tissues or cells by isolating said explants, tissues or cells and growing them in culture with specific soluble and insoluble inducers for sufficient periods of time to allow the cultured specimens to form multiple branches. The tips of these branches are then dissected out and recultured in the presence of serum, growth factor mix, mixture of conditioned and nutrient-rich medium for several generations to form 3-dimensional tubulogenic structures with multiple growing tips. This process can proceed ad infinitum under proper culture conditions having effective inducer substances.

The contemplated method further involves culturing and propagating embryonic mesenchymal tissues capable of inducing limited differentiation and directional growth to form functional organs or tissues. The mesenchymal or other inducing tissue fragments are dissected out at the time of induction, and cultured in the presence of serum, growth factor mix, and a mixture of appropriate conditioned medium and nutrient-rich medium. After several passages in primary culture, growing inductive tissue may be partitioned into multiple fragments. Each fragment can then grown separately in culture. Vasculogenesis within each fragment is induced by substrate deprivation and/or the addition of specific soluble factors.

Finally, a grown, vascularized tissue fragment is combined in coculture with a cultured tubulogenic fragment described hereinabove, in a matrix in which in vitro angiogenesis has begun. The two tissue fragments are grown in nutrient-rich medium conditions to enable continued vasculogenesis. Alternatively, the "cloned" kidney can be implanted for in vivo vascularization.

A more specific and preferred embodiment of this invention is a method for generating a functional mammalian kidney in vitro by culturing and propagating ureteric bud tissue. This method comprises isolating embryonic kidney rudiments by dissection, isolating ureteric bud tissue fragments from mesenchyme by incubating the kidney rudiments with a proteolytic enzyme in the presence of DNAase and/or by mechanical separation. The isolated ureteric bud fragments are suspended in a gel matrix and the gel/fragment composition is placed on porous polycarbonate membrane inserts in wells of tissue culture plates. Growth factors are added to the culture wells, and the gel composition comprising the bud fragments is maintained at the interface of air and medium until the fragments form multiple tubular branches inside the gel matrix. Individual distal branch tips formed during culture are dissected out and recultured in the presence of serum, growth factor mix, mixture of mesenchymal and ureteric bud cell conditioned medium and nutrient-rich medium for several generations.

The mechanical separation of tissue fragments can be accomplished by manual dissection or laser separation and capture. The growth factor mix includes glial cell line-derived neurotrophic factor or functional equivalent thereof. The added conditioned medium contains a heretofore-unidentified growth promoting constituent and/or inducer of differentiation. The extracellular matrix gel comprises a mixture of type I collagen and Matrigel or a comparable support matrix.

An equally preferred embodiment in accordance with this invention is method for simultaneous in vitro culturing and propagation of metanephric mesenchyme. This method comprises dissecting out fetal kidney mesenchyme tissue at the time of induction, culturing fragments of the mesenchymal tissue in the presence of serum, growth factor mix, mixture of mesenchymal and bud cell conditioned medium and nutrient-rich medium, and partitioning the cultured mesenchyme into multiple pieces. Each piece is grown separately in culture for several generations and grown mesenchyme is then subjected to substrate deprivation and/or additional growth factors in order to induce vasculogenesis.

A most preferred embodiment in accordance with this invention is a method for in vitro engineering and constructing a functioning mammalian kidney by culturing and propagating an isolated ureteric bud, permitting the cultured bud to form multiple branches, dissecting out the individual branch tips, and reculturing in the presence of serum, growth factor mix, mixture of mesenchymal and bud cell conditioned medium and nutrient-rich medium for several generations. The method also comprises simultaneously culturing and propagating isolated embryonic or fetal metanephric mesenchyme by dissecting out fetal mesenchyme at the time of induction, culturing mesenchymal tissue in the presence of serum, growth factor mix, mixture of mesenchymal and bud cell conditioned medium and nutrient-rich medium, potentially partitioning the mesenchyme into multiple pieces with the option of growing each piece separately, and inducing vasculogenesis by subjecting grown mesenchyme to substrate deprivation. The most preferred method then provides for recombining each vascularized mesenchyme piece with each cultured bud in a matrix in which in vitro angiogenesis has begun, and growing in richest medium conditions to ensure continued vasculogenesis.

Thus, in the most preferred embodiment, is a functional mammalian kidney constructed from isolated embryonic or fetal kidney tissue or cells cultured in rich medium that has present a mixture of growth factors and inducer substances, and comprises recombination of an isolated ureteric bud propagated in culture to produce a functioning nephron, and metanephric mesenchyme propagated from cultured embryonic mesenchymal tissue fragments or cells. Said mesenchyme has the capability of inducing differentiation and providing directional guidance to the branching tubulogenic bud.

Still further embodiments and advantages of the invention will become apparent to those skilled in the art upon reading the entire disclosure contained herein.

DESCRIPTION OF THE PREFERRED EMBODIMENTS

1. Introduction

Figure 1:
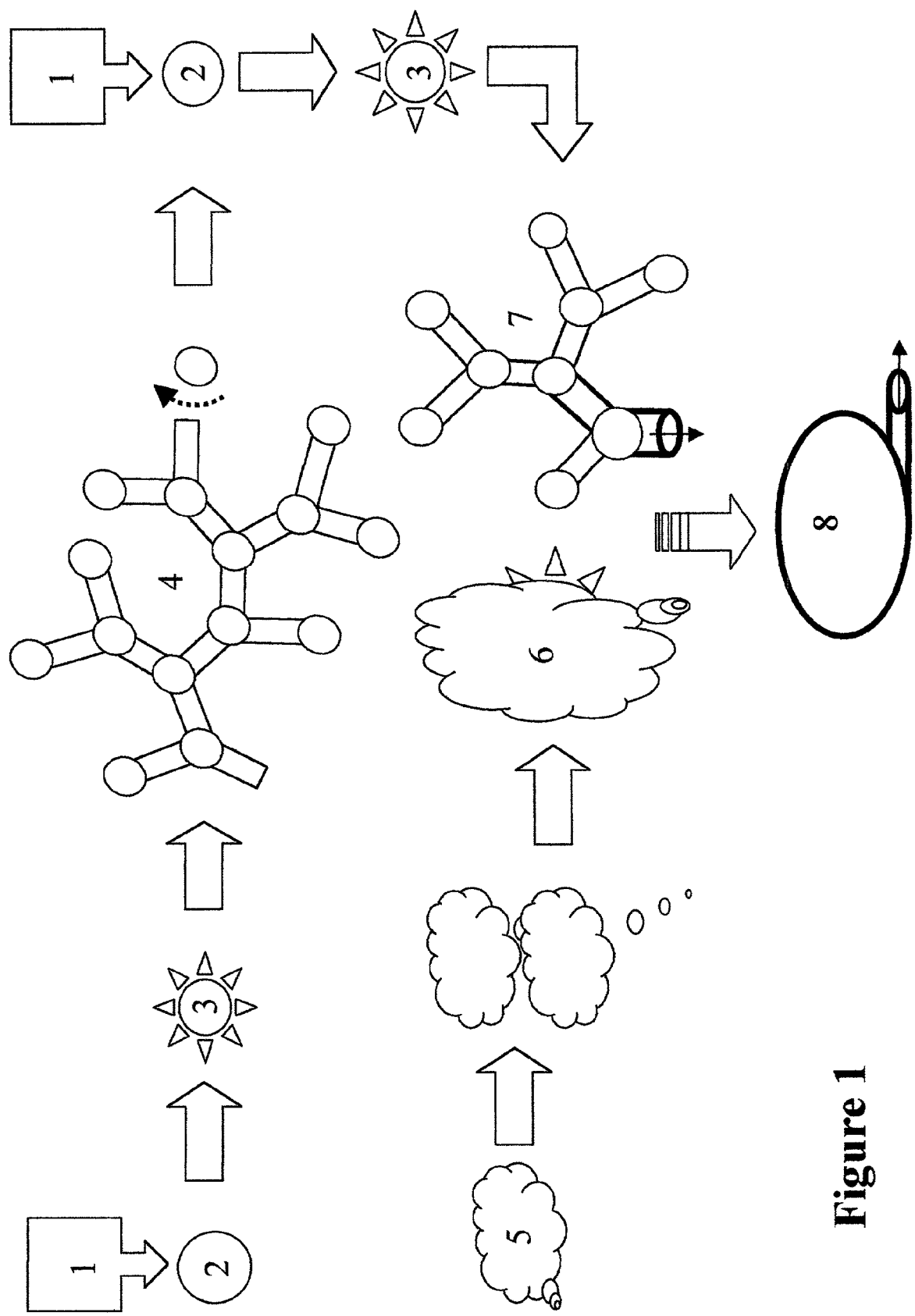
FIG. 1: A schematic representation of the methodology and salient points of this invention. A schematic diagram showing a novel culture method for inducing in vitro branching morphogenesis of an isolated ureteric bud (UB), simultaneous culture of mesenchymal tissue and recombination and coculturing of the two cultured tissue fragments. The mesenchymal tissue added to the bud culture induces the bud to directionally extend branching tubules and further differentiate and incorporate to form a functioning nephron, capable of absorbing, filtering, collecting and secreting body fluids. Schematically depicted is a ureteric bud fragment in culture 2, being induced by a stimulant(s) to produce a pluripotent fragment 3, that is capable of branching morphogenesis to form a branched three-dimensional structure 4. It can be see that an excised growing tip 2 can be further cultured in the presence of an inducer(s) 1 to again form an activated fragment 3, that will continue its tubulogenic morphogenesis. Simultaneously, an isolated fragment of mesenchymal tissue 5 is grown in culture to produce multiple pieces of mesenchymal tissue. One such piece 6 is grown and is then placed in coculture with an actively branching bud fragment 7. The bud fragment, under influence of the mesenchymal induction continues to branch in a now directed fashion and to further differentiate to form maturing effluent collecting tubules, enlarging as the branching progresses to accommodate increased effluent and incorporating into new nephrons. Eventually an embryonic kidney, or a functionally equivalent fragment thereof, is formed 8.

In vitro cell and organ culture models for the study of collecting system development.

Several in vitro cell culture models of tubulogenesis and branching morphogenesis can be used to perform cellular and molecular analyses of these processes that can not be easily accomplished with other models for urinary tract development.

Many techniques have been used to gain insight into the cellular and molecular basis of nephrogenesis. These include genetic approaches (knockouts and transgenics), organ culture and cell culture models. Now, it is clear that each of these approaches has limitations, and it is likely that only through their combined use that the field will arrive at an accurate picture of kidney and urinary tract development. With respect to collecting system development, it is difficult to analyze the molecular processes involved in tubulogenesis and branching morphogenesis in whole animals or whole embryonic kidney organ culture, given the spatiotemporal complexity of kidney development and multiple potential interactions between numerous mesenchymally and epithelial-derived cells in varying stages of differentiation. Until a few years ago, there were no simple in vitro systems to study tubulogenesis and branching of renal or renal-derived epithelial cells. In recent years, it has become possible to analyze these processes using renal epithelial cells cultured in extracellular matrix gels under stimulation by soluble growth factors and/or conditioned medium from cells derived from the early metanephric mesenchyme.

Hepatocyte growth factor (HGF), the receptor for which is c-met, a RTK, has been known for some time to be able to induce the formation of branching tubular structures when MDCK cells (a renal epithelial cell line) are seeded in Type I collagen matrix gels. Without HGF, these cells develop into cystic structures, but in the presence of HGF, the cells form cytoplasmic processes which eventually develop multicellular branching chords and then into tubular structures. The inventors have previously demonstrated that the HGF-induced structures have apical-basolateral polarity, as determined by immunofluorescence with antisera against marker proteins for apical and basolateral surfaces of polarized tubular epithelial cells (Dev. Biol., 159, 535–548, 1993). Thus, HGF is sufficient, in the setting of the appropriate three dimensional extracellular matrix, to produce polarized tubular structures similar to those existing in the differentiated collecting ducts (Dev. Biol., 160, 293–302, 1993; Dev. Biol. 163, 525–529, 1993, Proc. Natl. Acad. Sci., 92, 4412–4416). The inventors have also developed novel cell culture models for branching tubulogenesis using both mature collecting duct cells and embryonic ureteric bud cells. The morphogenesis of embryonic UB cells is largely dependent upon growth factors other than HGF.

Nevertheless, as inventors show below, inventors have, for the first time, been able to demonstrate that the isolated ureteric bud can undergo impressive branching morphogenesis in the presence of soluble factors, though there is a subsequent requirement for contact with mesenchyme for both elongation and guidance of branching ureteric-bud derived structures, as well as nephron formation. Thus, the inventors have set up unique embryonic cell and organ culture based systems that can help dissect the cellular and molecular basis of kidney growth, morphogenesis and development. Many of these systems were first established by the inventors and have been exclusively characterized by them. Several of these systems are described below.

EXAMPLE 1

Isolation of ureteric bud (UB) epithelium and UB culture (Proc. Natl. Acad. Sci., 86, 7330–7335, 1999 incorporated herein by reference): Kidney rudiments were dissected from timed pregnant Sprague Dawley rats at gestation day 13. (The plug day was designated as day 0). The UB was isolated from mesenchyme by incubating kidney rudiments in 0.1% trypsin in the presence of 50 U/ml DNAase at 37° C. for 15 minutes, and by mechanical separation with two fine-tipped minutia pins. For culture, Transwell tissue culture plates and a polycarbonate membrane insert with 3 um pore size were used. The extracellular matrix (ECM) gel (a mixture of type I collagen and Matrigel) was applied on top of the Transwell insert. Isolated UB was suspended in the ECM gel and cultured at the interface of air and medium. All cultures were carried out at 37° C. with 5% $CO_2$ and 100% humidity in DMEM/F12 supplemented with 10% Fetal Calf Serum (FCS). Growth factors were added as indicated elsewhere. Culture media were changed weekly if necessary.

EXAMPLE 2

Cells and conditioned media: The BSN cell line was derived from day 11.5 mouse embryonic kidney metanephric mesenchyme originally obtained from a mouse line transgenic fro the early region of SV-40/large T antigen. As described elsewhere, the BSN cells express the mesenchymal protein marker vimentin, but not classic epithelial marker proteins such as cytokeratin, ZO-1 and E-cadherin. Differences in the expression patterns of 588 genes in BSN cells have been analyzed by the inventors on commercially available cDNA grids (Am. J. Physiol.—Renal Physiol., 277, F:650–F663, 1999), and confirmed the largely non-epithelial character of BSN-cells, though it remains to be determined whether they are mesenchymal or stromal, or have characteristics of both cell types. The SV-40/large T antigen transformed UB cell line and murine inner-medulla collecting duct (mIMCD) cells have been extensively characterized before. To obtain conditioned media, a confluent cell monolayer was washed with serum-free medium, and then cultured in serum free medium for another 2–4 days. Various conditioned media were harvested after low speed centrifugation to remove cell debris and the concentrated 10-fold with a Centricon filter with 8 kDa nominal molecular weight cutoff (Millipore, Bedford, Mass.). In addition, BSN-CM was subfractioned on a heparin-sepharose affinity column (Hitrap Heparin; Pharmacia, NJ). Concentrated BSN-CM (~10X) was applied to a heparin column. After washing the column with Hanks' balanced buffer solution, the heparin bound fraction was eluted with 2 M NaCl in Hanks' balanced buffer solution. After desalting with a PD-10 column (Pharmacia, NJ), the heparin bound fraction's final volume was adjusted to the starting volume. The heparin flow through fraction was collected and its volume was adjusted to the starting volume using a Centricon filter (8 kDa cutoff). The partially purified fractions were assayed for their effect on UB morphogenesis in the presence of GDNF.

EXAMPLE 3

The ECM gel mix: The ECM gel mix was composed of 50% type I collagen (Collaborative Biomedical Product) and 50% growth factor-reduced Matrigel® (Collaborative Biomedical Product). The procedure for gelation has been previously described in detail and is incorporated herein.

EXAMPLE 4

Induction of nephrogenesis by cultured UB: Isolated UBs were first cultured for 7–10 days as already described. Then, the cultured UB was isolated from the ECM gel by incubation with collagenase (1 mg/ml) and dispase (2 ml/ml) at 37° C. for 30 minutes, followed by mechanical separation with fine tipped minutia pins. The UB was then recombined with freshly isolated E-13 rat metanephric mesenchyme and co-cultured on a transfilter for another 5 days in DMEM/F12, plus 10% FCS.

EXAMPLE 5

Lectin staining: 1) Dolichos Bioflorus (DB) lectin: Tissues were fixed with 2% paraformaldehyde for 30 minutes at 4° C., permeabilized with 0.1% Saponin and then incubated with fluorescent conjugated DB (50 ug/ml, Vector) in a moisturized chamber for 60 minutes at 37° C. After extensive washing, tissues were post-fixed in 2% paraformaldehyde again for 5 minutes and viewed using a laser scanning confocal microscope. The specificity of DB lectin binding has been demonstrated previously. 2) Peanut agglutinin (PNA) lectin: Tissues were fixed with 2% paraformaldehyde for 30 minutes at 4° C.; blocked with 50 mM $NH_4Cl$ overnight at 4° C., followed by an incubation with 1% gelatin in 0.075% Saponin for 30 minutes at 37° C. After two washes with Neuraminidase buffer (150 mM NaCl, 50 mM Na-Acetate, pH 5.5), tissues were incubated with Neuraminidase (1 U/ml) for 4 hours at 37° C. and then with Rhodamine-conjugated PNA (50 ug/ml) for 60 minutes at 37° C. Tissues were post-fixed with 2% paraformaldehyde and viewed with a laser scanning confocal microscope.

EXAMPLE 6

Immunocytochemistry: Tissues were fixed with either 2% paraformaldehyde at 4° C. or 100% methanol at −20° C. Tissues were permeablized with 0.1% Saponin and non-specific binding was blocked with fetal 100% FCS***. The incubations with primary and secondary antibodies were carried out for 60 minutes at 37° C. The staining with FITC or TRITC-conjugated antibodies was viewed with a laser scanning confocal microscope.

EXAMPLE 7

Confocal Analysis: Confocal images were collected with a laser scanning confocal microscope (Bio-Rad MRC 1024, Bio-Rad, CA). Each three-dimensional picture was reconstructed from a set of 10 um serial sections, which spanned the tissue. Images were processed with Laser Sharp™ (Bio-Rad) and Photoshop™ (Adobe, CA) software.

DISCUSSION

The abovementioned examples define a new method of producing an active, functional embryonic kidney or fragment.

Figure 2:
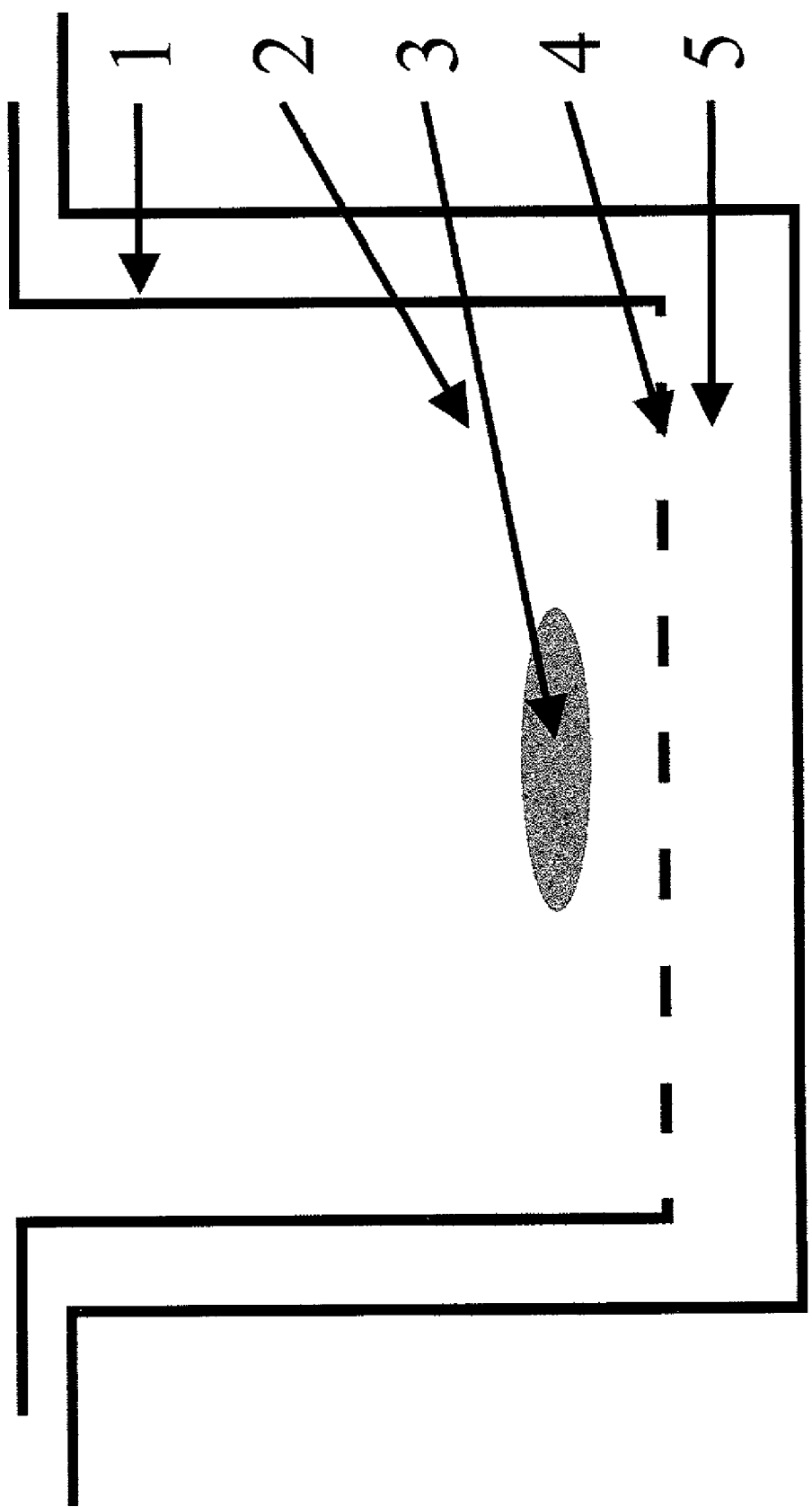
FIG. 2: A novel culture system for in vitro branching morphogenesis of the ureteric bud (UB) (Proc. Natl. Acad. Sci., 96, 7330–7335, 1999 incorporated herein by reference—please refer to this paper for color reproductions). UBs free from mesenchyme were micro-dissected from E-13 rat kidney rudiments and placed in an ECM gel suspension composed of type I collagen and growth factor-reduced Matrigel®, and cultured in BSN cell-conditioned medium (BSN-CM) supplemented with 10% FCS and growth factors. Details are given elsewhere in the text. The cultured UB was monitored daily by microscopy. Shown in the figure is transwell insert (1), ECM gel (2), isolated UB (3), polycarbonate filter (4), and BSN-CM plus growth factor(s) (5).
Figure 3:
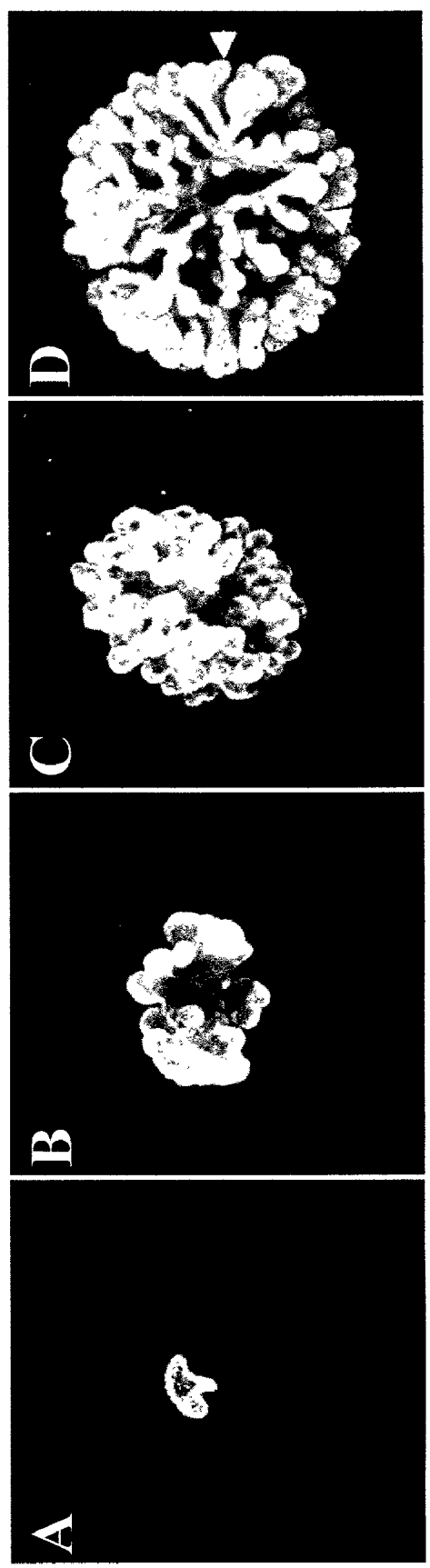
FIG. 3: The UB undergoes branching morphogenesis in vitro and develops three-dimensional tubular structures in the absence of mesenchyme (Proc. Natl. Acad. Sci., 96, 7330–7335, 1999 incorporated herein by reference-please refer to this paper for color reproductions). E-13 rat UB was isolated and cultured as described herein below. After culture, UBs were fixed at different time points and processed for DB lectin staining. 3-D reconstructions of confocal images are shown: a) A freshly isolated UB from an E-13 rat embryonic kidney with a single branched tubular structure; b) The very same UB shown in a) after being cultured for 3 days. The tissue has proliferated and small protrusions have formed; c) Again, the same UB as shown in a) cultured for 6 days. More protrusions have formed, and the protrusions have started to elongate and branch dichotomously; d) the same UB as shown in a) cultured for 12 days. The protrusions have undergone further elongation and repeated dichotomous branching to form a structure resembling the developing collecting system of a kidney. The white arrows indicate branch points. At higher power, the structures formed in this in vitro culture system exhibited lumens. Phase microscopic examination and staining for markers revealed no evidence for contamination by other tissue or cells.

Immortalized UB cells have been shown by the inventors to undergo impressive morphogenesis in the presence of soluble factors (16) when seeded in extracellular matrix gels containing Type I collagen mixed with growth factor-depleted Matrigel®, a basement membrane extract derived fro EHS sarcoma cells (Proc. Natl. Acad. Sci., 86, 7330–7335, 1999 incorporated herein by reference). A conditioned medium elaborated by BSN cells (BSN-CM), an immortalized line derived from early metanephric mesenchyme that has been developed by the inventors, has been shown to induce the formation of branching tubular structures, some of which have apparent lumens; the key activity in BSN-CM was shown to be distinct from a number of growth factors known to induce morphogenesis in mature kidney epithelial cell lines. The results from these cell culture studies suggest that the program for branching morphogenesis exists within UB cells and does not require direct contact with metanephric mesenchymal cells. Reasoning that the conditions for branching morphogenesis of isolated UB tissue might be similar to this in vitro cell culture system employing a UB cell line, the inventors separated embryonic rat kidney UB from the metanephric mesenchyme prior to induction and cultured the isolated UB (free from mesenchyme) in a mixture of collagen and growth factor deleted Matrigel® (FIG. 2). After trying many different conditions, dichotomous branching morphogenesis resembling the structures of the developing embryonic kidney was achieved when the isolated UB was cultured in the presence of a combination of BSN-CM and a mixture of growth factors (EGF, HGF, IGF, FGF-2 and GDNF) (FIG. 3). The growth factor mixture was chosen based upon the effects of individual factors on in vitro morphogenesis of cultured UB and mIMCD cells previously performed by the inventors; HGF and EGF induce complex morphogenetic changes in UB and mIMCD cells, while IGF and FGF-2 induce some morphogenetic changes in UB cells. Because of strong genetic and cell culture data supporting the role of GDNF/cRET in early UB morphogenesis and survival of UB-derived cells, GDNF was also added to the mixture.

At gestational day 13, rat UB is a "T" shaped epithelial tubule (FIG. 3a). In vivo, this single branched epithelial tubule undergoes repeated dichotomous branching and forms the "tree" shaped collecting system through interactions with metanephric mesenchyme. This epithelial-mesenchymal interaction is thought to be required for the tubular/ductal development of several organ systems, such as lung, pancreas and mammary gland. In the inventors' system, isolated UB (free from metanephric mesenchyme) can be cultured and induced to undergo branching morphogenesis in vitro. The cultured UB branched dichotomously with formation of structures that had apparent lumens. Each branch had both tubular and ampullary portions (FIG. 3b through d). Staining with lectins and antibodies indicated that the tubular structures remained UB-derived and epithelial in character. Both cell proliferation and branching morphogenesis appeared to occur simultaneously. In most cases, after 48 hours of culture, UB epithelial tissue started to increase in size and developed small protrusions from the "T" shaped ureteric bud. After 3–4 days of culture, those protrusions started to elongate, and the tips of the elongated structure started to branch dichotomously. The structures formed form the cultured UB revealed no staining with vimentin antibodies and peanut lectin (PNA), markers for mesenchymally derived elements, further supporting the notion that, in the appropriate milieu of soluble factors, complex branching of the UB can occur in the absence of direct contact with the metanephric mesenchyme. Moreover, growth of isolated UB was observed for up to 3–4 weeks, with many generations of branching.

Figure 4:
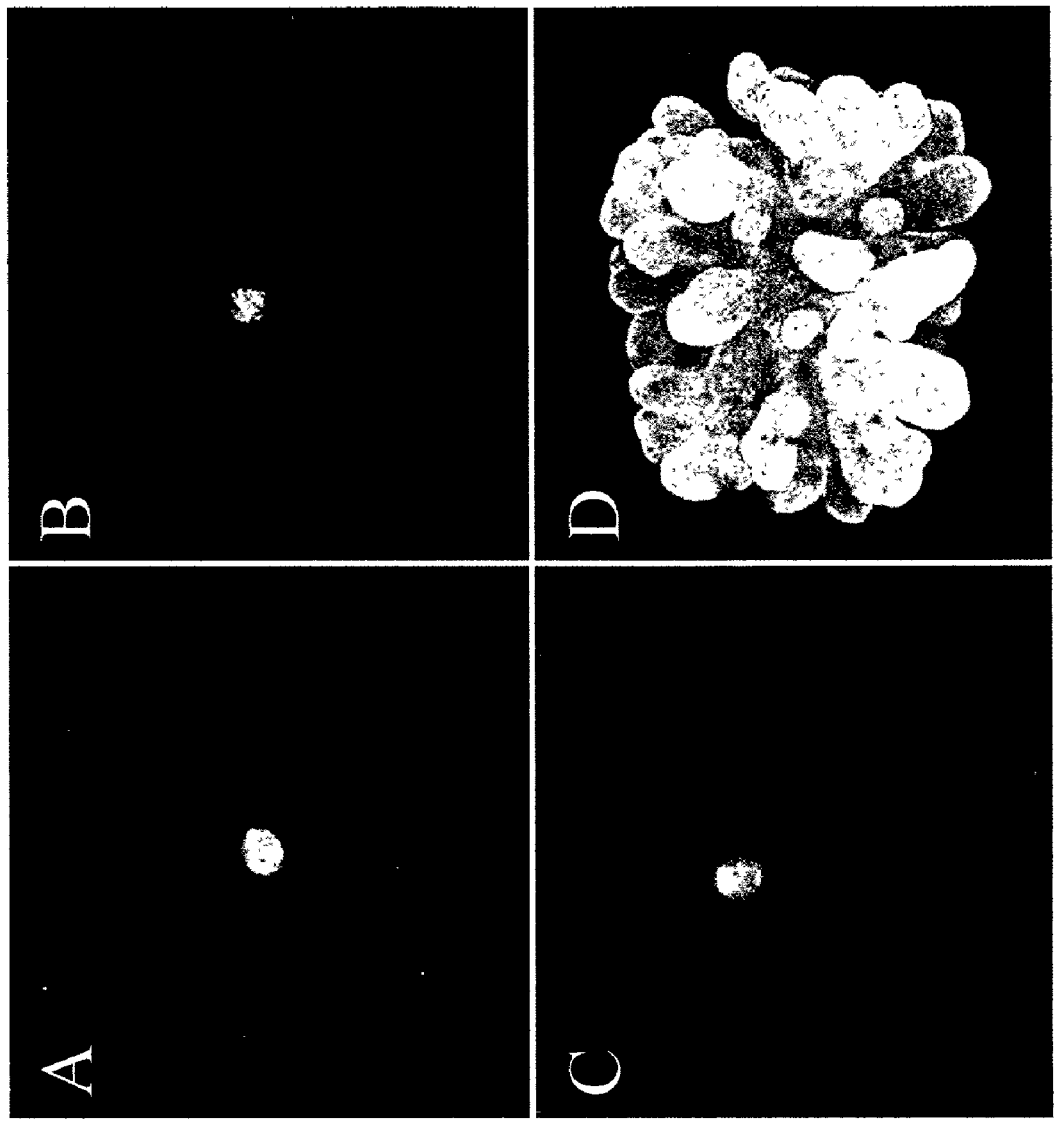
FIG. 4: BSN-CM and at least one soluble growth factor are required for branching morphogenesis of the isolated UB (Proc. Natl. Acad. Sci., 96, 7330–7335, 1999 incorporated herein by reference-please refer to this paper for color reproductions). A: The UB cultured in the absence of BSN-CM and growth factors; B: The UB cultured with the mixture of growth factors (including EGF, IGF, HGF, FGF-2, and GDNF) but no BSN-CM; C: The UB cultured in the presence of BSN-CM alone; D: The UB cultured in the presence of both BSN-CM and the mixture of growth factors. All cultures were carried out for about one week and then processed for DB lectin staining. Shown is the three-dimensional reconstruction of confocal images. The isolated UB exhibits branching morphogenesis only in the presence of both BSN-CM and the mixture of growth factors.
Figure 5:
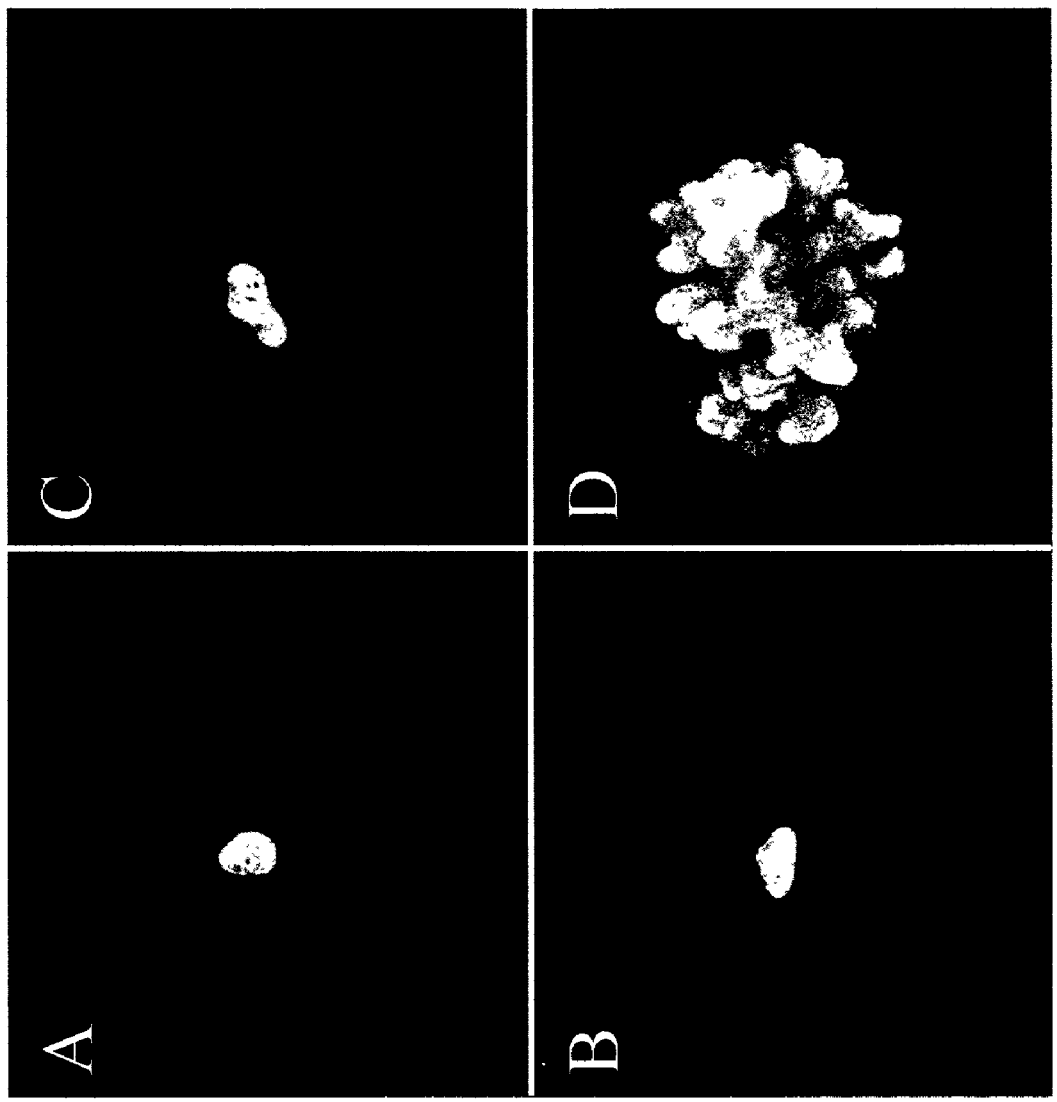
FIG. 5: BSN-CM contains unique soluble factor(s) for branching morphogenesis of the isolated UB (Proc. Natl. Acad. Sci., 96, 7330–7335, 1999 incorporated herein by reference-please refer to this paper for color reproductions). The UBs were cultured in the presence of the key growth factor (GDNF; see FIG. 7) but with different cell conditioned media: A: 3T3 fibroblast cell conditioned medium; B: immortalized UB cell conditioned medium; C: mIMCD cell conditioned medium; D: BSN cell conditioned medium. After culture, the UBs were fixed and processed for DB lectin staining. Only BSN-CM could promote extensive branching morphogenesis of the isolated UB.
Figure 6:
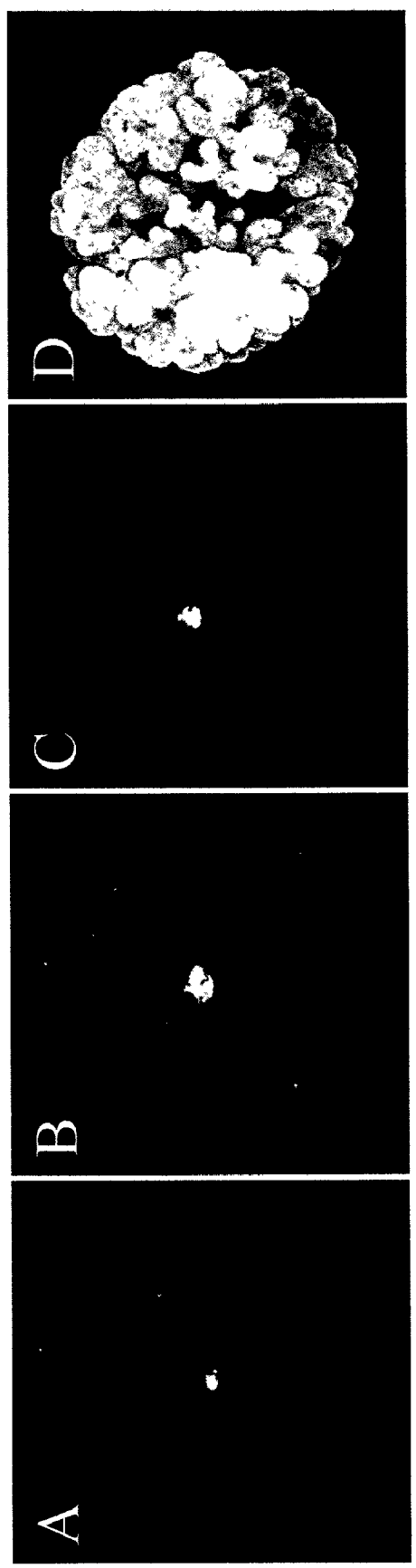
FIG. 6: GDNF plus BSN-CM is required for branching morphogenesis (Proc. Natl. Acad. Sci., 96, 7330–7335, 1999 incorporated herein by reference-please refer to this paper for color reproductions). The UBs were cultured in the presence of BSN-CM, as in FIG. 4 but with each of single growth factors present in the growth factor mixture. Several examples are shown: A: with EGF alone; B: with FGF-2 alone; C: with HGF alone; D: with GDNF alone. Only GDNF combined with BSN-CM could promote branching morphogenesis of the isolated UB.

BSN-CM played a critical role in this morphogenetic process (FIGS. 4A–D). In the absence of BSN-CM, growth factors had no effect on proliferation and branching morphogenesis of the UB (FIG. 4B). Only when BSN-CM was present, did the UB develop into a three-dimensional tubular structure (FIGS. 4D and 5D). To examine whether BSN-CM contained unique factors for the branching morphogenesis of the UB, conditioned media from different cell lines were compared. Neither conditioned medium derived from Swiss 3T3 fibroblasts (an inducer of MDCK cell branching tubulogenesis in Type I collagen) nor from UB cells or mIMCD3 cells was capable of substituting for BSN-CM (FIGS. 5A–C), suggesting that the BSN cells retain the ability to secrete a relatively unique factor, or set of factors, made by the metanephric mesenchyme and required for UB branching morphogenesis (FIG. 5D). This activity was heat-sensitive. When BSN-CM was fractionated over a heparin sepharose column, only the heparin bound fraction exhibited morphogenetic activity.

Figure 7:
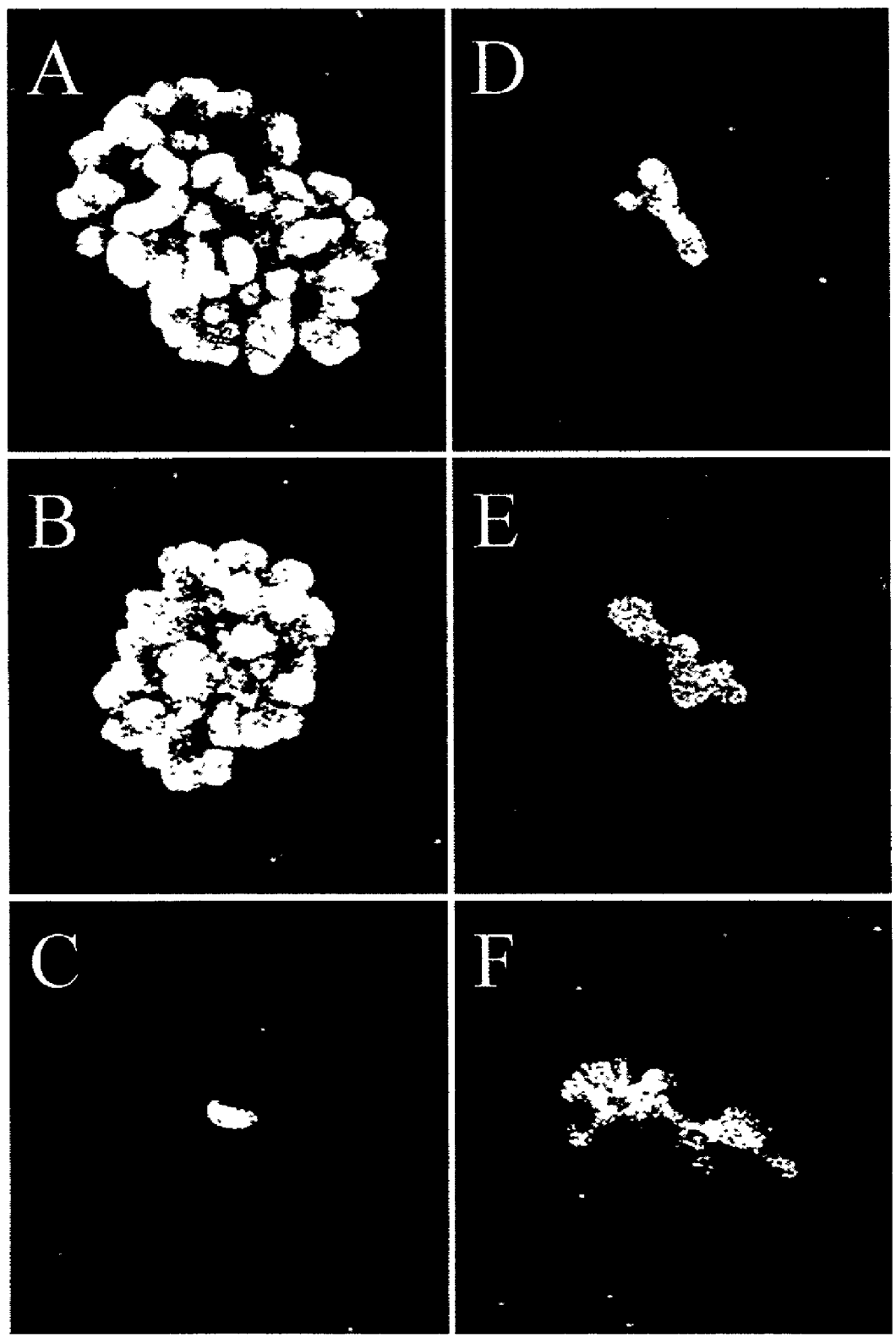
FIG. 7: GDNF is required for both early and late branching morphogenesis in vitro. (Proc. Natl. Acad. Sci., 96, 7330–7335, 1999 incorporated herein by reference-please refer to this paper for color reproductions) A–C: The antibodies against GDNF are neutralizing antibodies. A: UB was cultured in the presence of BSN-CM and GDNF without antibodies; B: same as A, but normal goat IgG antibody were added; C: same as A, but antibodies against GDNF were added. D–F: GDNF is required for branching morphogenesis. The UBs were initially cultured in the presence of BSN-CM and GDNF and then the cultures were washed to remove GDNF at different time points; the UBs were then continuously cultured in BSN-CM without GDNF. To ensure neutralization of residual GDNF in the culture, antibodies against GDNF were added after removal and washing of GDNF from the culture medium. D: The UB was cultured as in A, but GDNF was removed and antibodies against GDNF were added on the first day of culture; E: Same as D, but the GDNF was removed and antibodies against GDNF were added on the second day of culture; F: Same as D, but the GDNF was removed and antibodies against GDNF were added on the third day of culture (compare with structures in FIG. 3). All cultures were carried out until the fifth day and processed with DB lectin staining. Whenever GDNF is depleted, UB growth and branching morphogenesis is aborted, indicating that GDNF is required for both early and late branching morphogenesis in vitro.

Nevertheless, the factor (or a set of factors) in BSN-CM was not sufficient to induce UB branching morphogenesis. In the absence of the growth factor mixture, the UB underwent apoptosis as determined by the TUNEL assay (data not shown). To further define conditions for in vitro UB branching morphogenesis, the Inventors examined whether any single growth factor present in the growth factor mixture could, in combination with BSN-CM, induce UB branching morphogenesis. The combination of BSN-CM and GDNF, but no other combination, was found to be sufficient to induce the formation of three-dimensional branching structures comparable to those observed with BSN-CM and the growth factor mixture (FIGS. 6A–D). Consistent with this observation, the combination of BSN-CM and GDNF prevented the UB from undergoing apoptosis and facilitated UB proliferation (data not shown). Since GDNF alone could not induce branching morphogenesis in the absence of BSN-CM, a factor or factors present in the BSN-CM must be required for the action of GDNF in the induction of UB branching morphogenesis. While studies from others have indicated that GDNF is involved in the initial formation of the UB , it has not been established whether GDNF is required for the further ranching morphogenesis of the UB. Therefore, the UB was first cultured in the presence of BSN-CM and GDNF, and then in the absence of GDNF after repeatedly washing away GDNF from the culture and then adding antibodies know to neutralize GDNF in the system (FIGS. 7A–C). Withdrawal of GDNF from the culture system blocked further UB branching morphogenesis, suggesting that GDNF is not only involved in early UB formation but also in further iterations of UB branching (FIG. 7D–F and compare FIGS. 7E and 7F with FIGS. 3b and 3c). In this regard, it is interesting to note that mesenchymal cell contact or some other soluble factor may be able to partially compensate for GDNF, at least under certain conditions in whole organ culture, since c-RET antisense oligonucleotides are not strongly inhibitory of continued branching of the UB when added after induction.

Figure 8:
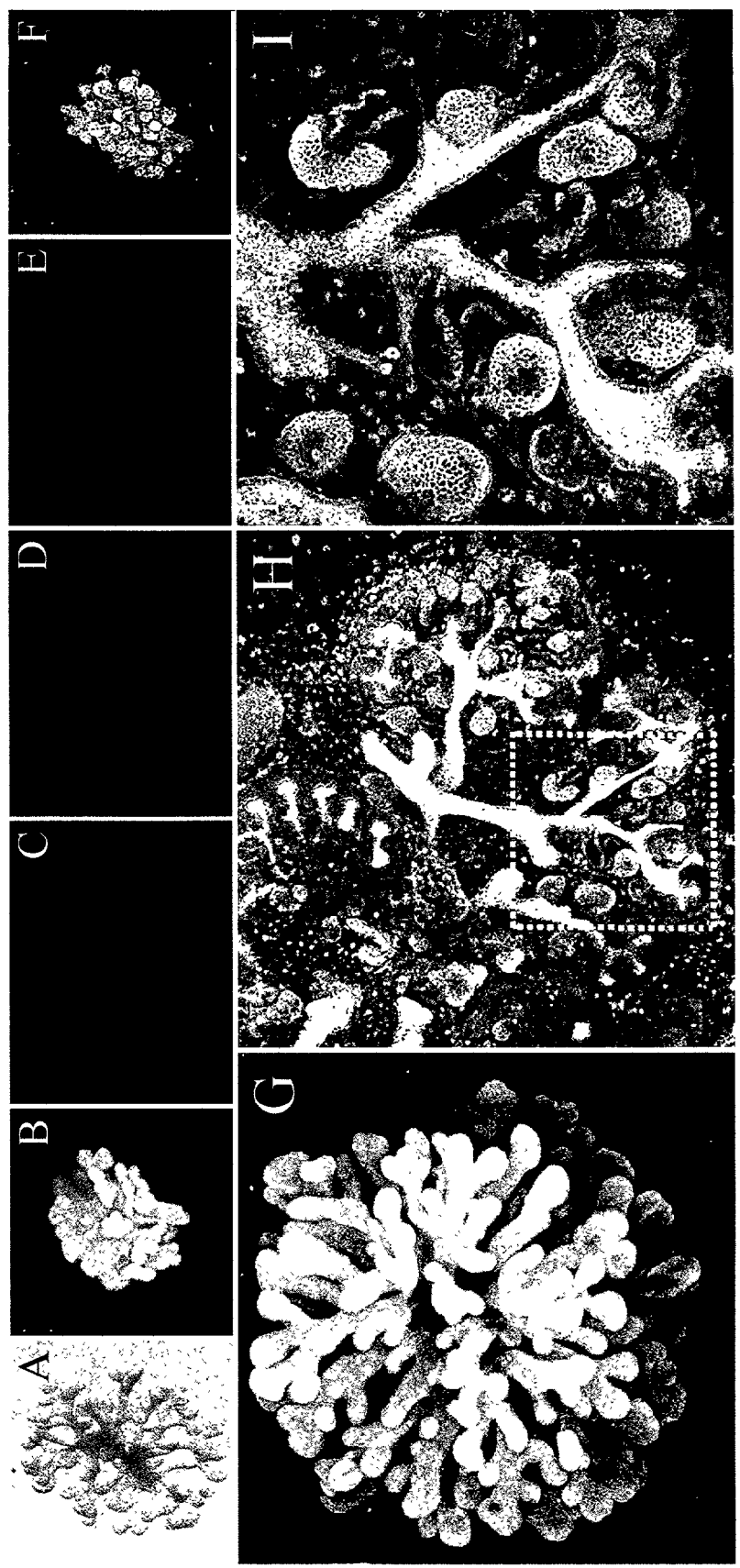
FIG. 8: The cultured three-dimensional tubular structure exhibits markers of UB epithelium and is functionally capable of inducing nephrogenesis when recombined with metanephric mesenchyme in vitro. (Proc. Natl. Acad. Sci., 96, 7330–7335, 1999 incorporated herein by reference-please refer to this paper for color reproductions). The UBs were cultured in the presence of BSN-CM and GDNF and then stained for various markers (A–F). A: Light microscopic phase photograph of cultured UB; B: Staining with DB lectin, a ureteric bud specific lectin which binds to the UB and its derivatives; C: Staining for vimentin, a mesenchymal marker; D: Staining for N-CAM, the early marker for mesenchymal to epithelial conversion in the kidney; E: Staining with PNA lectin, a mesenchymally derived renal epithelial cell marker; F: Staining for cytokeratin, an epithelial marker. G–I: The cultured three-dimensional tubular structure is capable of inducing nephrogenesis when recombined with metanephric mesenchyme. The isolated UB was first cultured 7–10 days as shown in G. Then, the cultured UB was removed from the ECM gel and recombined with freshly isolated metanephric mesenchyme from E-13 rat kidneys. The recombinant was cultured on a Transwell filter for another 5 days. After culture, the sample was double stained with DB lectin (FITC) and PNA lectin (TRITC) as shown in H and in the enlarged section of H shown in I. Results indicate that the in vitro cultured UB derived structures are capable of inducing nephrogenesis in vitro.
Figure 9:
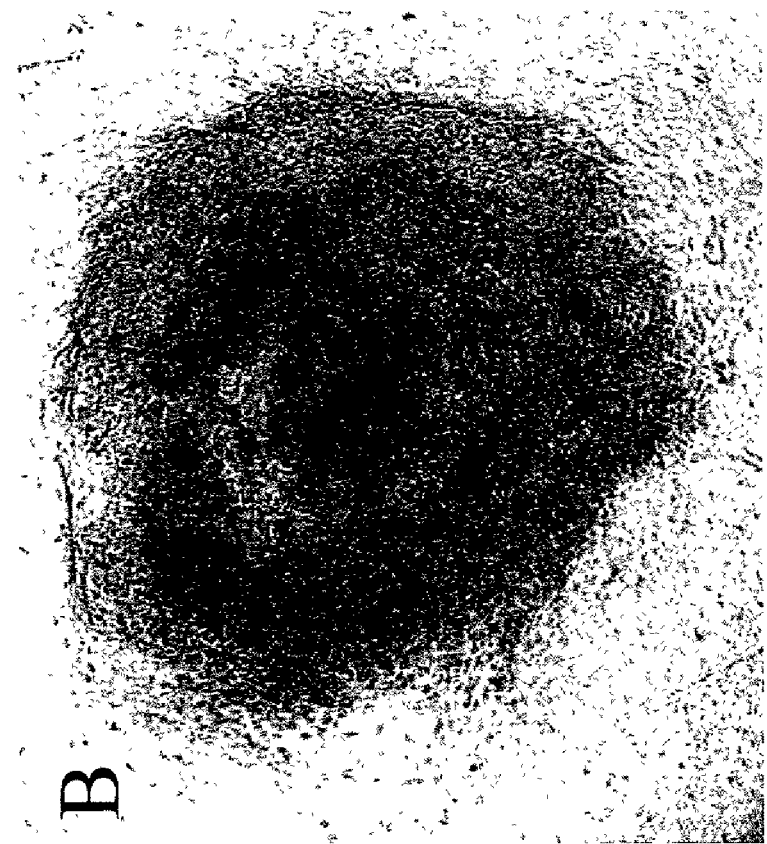
FIG. 9: Culture of metanephric mesenchyme. Day 13 embryonic rat kidneys rudiments were microdissected to separate the ureteric bud from the metanephric mesenchyme. The metanephric mesenchyme was then placed in a Transwell tissue culture insert on top of the polycarbonate filter (3 μm pore size). Media (DME/F12) supplemented with 10% fetal calf serum (FCS) was placed in the bottom of the chamber and the entire setup was incubated at 37° C. with 5% $CO_2$ with 100% humidity. (A) Freshly isolated metanephric mesenchyme. (B) The same metanephric mesenchyme following 5 days in culture.
Figure 9:
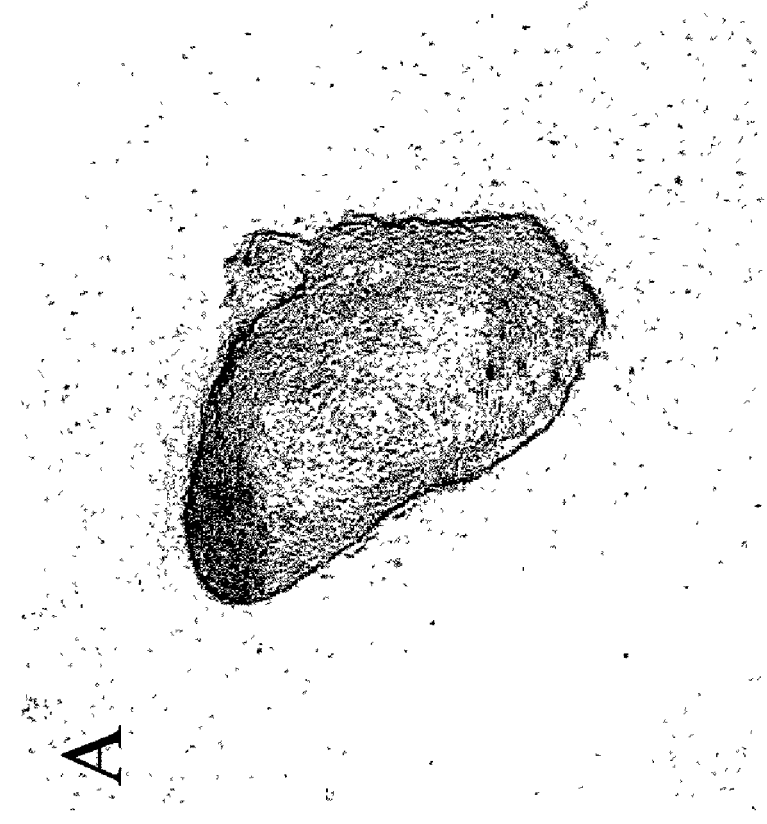
Figure 10:
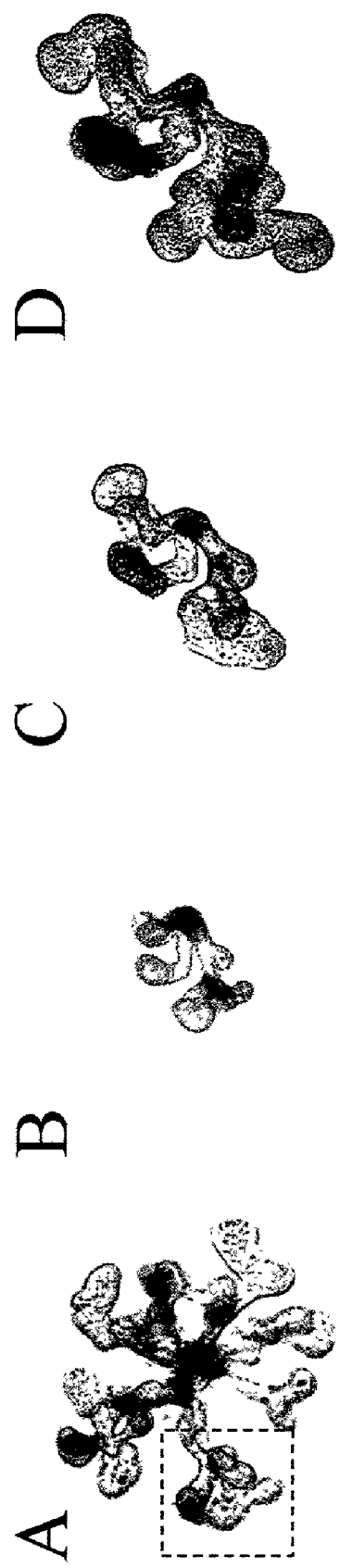
FIG. 10: Subculture of the ureteric bud. Ureteric buds were isolated from E13 rat kidneys and grown in culture for 7 days. At the end of this culture period the ureteric bud was dissected free of the surrounding extracellular matrix and the bud was cut into pieces and subcultured under the same conditions. (A) Originally isolated ureteric bud after seven days of culture. Black box indicates piece of bud that was dissected free and subcultured. (B) Subcultured bud after 24 hrs in culture. (C) Subcultured bud after 4 days in culture. (D) Subcultured bud after 7 days in culture.
Figure 11:
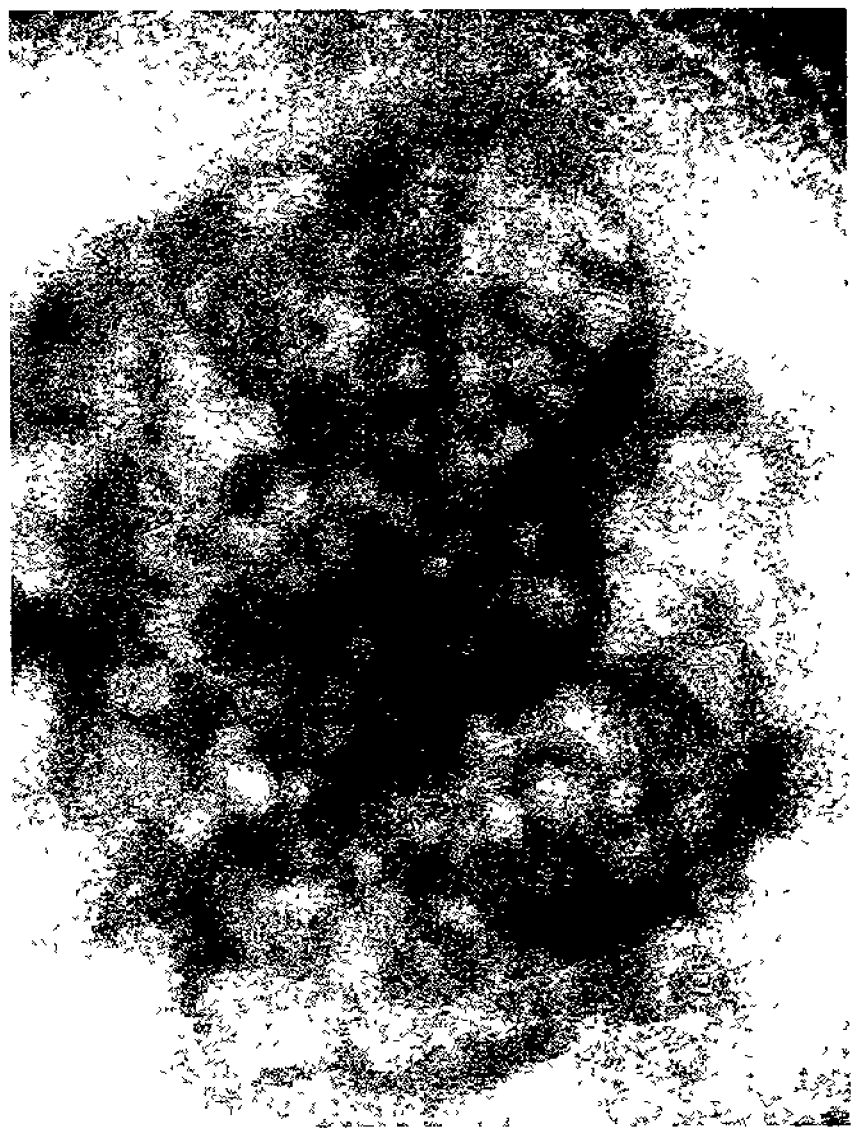
FIG. 11: Recombination of subcultured bud with freshly isolated metanephric mesenchyme. Ureteric buds were isolated, cultured and subcultured as previously described in FIG. 10. Metanephric mesenchymes were microdissected from E13 day rat embryonic kidneys and placed in close contact with subcultured ureteric bud as in FIG. 8. The recombined tissues were grown in culture for 7 days. Tubular structures are evident at this time.

To characterize the complex tubular structures of the in vitro cultured UB, expression of several markers was examined. The cultured UB structures exhibited positive staining with DB lectin and cytokeratin antibodies, but negative staining with PNA lectin and vimentin antibodies. The expression pattern of these markers confirmed that the tubular structures formed in vitro were UB-derived (FIGS. 8A–F). Nevertheless, a key issue was whether the cultured UB retained the capacity for induction of nephric units in the metanephric mesenchyme. When this was tested, it was confirmed that the tubular structures resulting from the cultured UB were capable of eliciting mesenchymally-derived metanephric nephronal structures and of being incorporated into the nephric unit when recombined with the freshly isolated metanephric mesenchyme (FIGS. 8G–I). As shown by PNA staining, most nephrons were located at the periphery of the cultured tissue, where tips of new UB branches were forming. All formed mesenchymally-derived nephronal structures appeared connected with the tubular structures of UB. In addition, the cultured UB structures continued to respond to the inductive effect of mesenchyme by elongating further into the mesenchymal tissue (FIGS. 8H–I). Together, these results indicate that the structures grown in vitro are UB-derived epithelial tubules and retain induction competence even after many days of ex vivo culture. The results also suggest that while the factor(s) in BSN-CM plus GDNF may be sufficient for the initial branching processes, later events in UB morphogenesis (e.g. elongation and establishing the pattern of branching) may require contact with mesenchyme.

Thus, by utilizing the Inventors' novel model system, the Inventors have found that, in contrast to the widely held view that the complex arborization of the UB during kidney development is dependent upon direct contact between cells of the metanephric mesenchyme and cells of the UB, a substantial degree of branching morphogenesis can be mediated by soluble factors lone. Therefore, the branching program exists within the UB itself after it is formed form the Wolffian Duct, and soluble factors can trigger its initiation and continuation. No singular soluble factor, however, appears sufficient. A combination of GDNF and an activity, or set of activities, present in BSN-CM is necessary. Whether this latter activity is the same as that which induces the formation of branching tubules with lumens of UB cells in culture remains to be determined. It seems very likely that more direct mesenchymal interactions with the UB are important for establishing the direction of branching events since the cultured UB-derived structures lack directionality, and only when the culture UB was recombined with metanephric mesenchyme did directionality and elongation occur (FIGS. 8H–I). Epithelial-mesenchymal cell-cell contact is probably essential for the later steps in the development of UB/collecting system. Additional mechanisms are likely to be involved in the formation of junctions between mesenchymally-derived nephronal segments and collecting tubules and the development of tertiary structures of the collecting tubule, such as the formation of arcades. Moreover, contact with the mesenchyme might provide a "stop" mechanism for kidney growth since Inventors found that the isolated UB continued to grow in vitro as long as soluble factors were provided.

Inventors' data also clarify the role of GDNF in kidney development. To date, GDNF has been implicated in initial UB outgrowth and early survival, but its role in branching morphogenesis of the UB has been debated. Inventors' data indicate that GDNF, in combination with factors in BSN-CM, supports true morphogenesis of the UB, at least in vitro. GDNF is required for not only the initial outgrowth but also the subsequent branching morphogenesis of the UB.

Finally, these results suggest that it be worth reevaluating the role of cell contact versus soluble factors in a wide variety of epithelial tissues where intimate cellular interactions between epithelial and mesenchymal tissues are thought to play a crucial inductive role, particularly with respect to branching morphogenesis. In the developing kidney, and perhaps in many of these other tissues, the role of cell contact may be facilatory rather than crucial for early branching morphogenesis per se, although it may be essential for the establishment of vectoriality and later events in differentiation (Proc. Natl. Acad. Sci., 86, 7330–7335, 1999 incorporated herein by reference).

While the present invention has now been described in terms of certain preferred embodiments, and exemplified with respect thereto, one skilled in the art will readily appreciate that various modifications, changes, omissions and substitutions may be made without departing from the spirit thereof. It is intended, therefore, that the present invention be limited solely by the scope of the following claims.

The invention claimed is:

1. A method for constructing a mammalian tissue or a fragment thereof in vitro, comprising:

(a) culturing and propagating embryonic epithelial-derived explants, tissue or cells comprising:
  (i) isolating the tissues or cells and growing them in culture,
  (ii) permitting the tissue or cells to form multiple branches,
  (iii) dissecting out individual branch tips,
  (iv) culturing the individual branch tips in the presence of nutrient medium, serum, at least one growth factor, and BSN-conditioned medium (BSN-CM) on an extracellular matrix (ECM) gel for several generations to generate branch tip buds;
(b) culturing and propagating isolated embryonic or fetal metanephric mesenchyme comprising:
  (i) dissecting out embryonic or fetal metanephric mesenchyme at the time of induction,
  (ii) culturing the embryonic or fetal metanephric mesenchymal tissue in the presence of nutrient medium, serum, at least one growth factor, and BSN-CM,
  (iii) partitioning mesenchyme into multiple pieces and culturing each piece separately, and
  (iv) inducing vasculogenesis by subjecting cultured mesenchyme to substrate deprivation or addition of soluble growth factors;
(c) combining each vascularized mesenchyme with each cultured branch tip bud in a matrix in which in vitro angiogenesis has begun such that the mesenchyme and tip bud are in close contact; and
(d) culturing the combined tissue under conditions to ensure continued cell growth to obtain a vascularized mammalian tissue,
wherein the at least one growth factor comprises glial cell line-derived neurotrophic factor (GDNF).

2. The method according to claim 1, wherein the at least one growth factor comprises a glial cell line-derived neurotrophic factor and at least one other growth factor selected from the group consisting of EGF, HGF, IFG, and FGF-2.

3. The method according to claim 1, wherein the extracellular matrix gel comprise a mixture of type I collagen and a basement membrane preparation.

4. The method according to claim 1, wherein the vascularized mammalian tissue is implanted into a recipient without prior induction of vasculogenesis.

5. The method of claim 1, wherein the vascularized mammalian tissue is mammalian kidney tissue.

* * * * *